United States Patent
Biali et al.

(10) Patent No.: US 6,465,005 B1
(45) Date of Patent: Oct. 15, 2002

(54) INHIBITION OF CRYSTALLIZATION IN TRANSDERMAL DEVICES

(75) Inventors: Fabián Isaac Biali, Buenos Aires (AR); Alejandro Fabio Scasso, Buenos Aires (AR); Francisco José Evaristo Stefano, Buenos Aires (AR)

(73) Assignee: Amarin Technologies S.A., Buenos Aires (AR)

( * ) Notice: Subject to any disclaimer, the term of this patent is extended or adjusted under 35 U.S.C. 154(b) by 0 days.

(21) Appl. No.: 09/509,122

(22) PCT Filed: Sep. 24, 1998

(86) PCT No.: PCT/GB98/02880

§ 371 (c)(1),
(2), (4) Date: May 17, 2000

(87) PCT Pub. No.: WO99/15156

PCT Pub. Date: Apr. 1, 1999

(30) Foreign Application Priority Data

Sep. 25, 1997 (GB) .............................................. 9720470

(51) Int. Cl.[7] .......................... A61F 13/00; A61F 15/16; A61K 9/14

(52) U.S. Cl. ....................... 424/449; 424/448; 424/443; 424/484

(58) Field of Search .................................. 424/449, 448, 424/443, 484

(56) References Cited

U.S. PATENT DOCUMENTS

| | | | |
|---|---|---|---|
| 4,814,168 A | 3/1989 | Sablotsky et al. | |
| 4,832,953 A | 5/1989 | Campbell et al. | |
| 5,023,084 A | 6/1991 | Chien et al. | |
| 5,223,261 A | 6/1993 | Nelson et al. | |
| 5,352,457 A | 10/1994 | Jenkins | |
| 5,460,820 A | * 10/1995 | Ebert et al. | |
| 5,518,734 A | 5/1996 | Stefano et al. | |
| 5,676,968 A | * 10/1997 | Lipp et al. | |
| 5,906,830 A | * 5/1999 | Farinas et al. | |

FOREIGN PATENT DOCUMENTS

| | | |
|---|---|---|
| DE | 4210711 | 5/1993 |
| EP | 0328806 | 8/1989 |
| EP | 0430491 | 6/1994 |
| EP | 0379045 | 5/1995 |
| WO | WO 89/07951 | 9/1989 |
| WO | WO 90/06120 | 6/1990 |
| WO | WO 95/18603 | 7/1995 |
| WO | WO 95/22322 | 8/1995 |
| WO | WO 96/05815 | 2/1996 |

OTHER PUBLICATIONS

Stefano et al., International Symposium. Control. Rel. Bioact. Mater., 24 (1997), p. 703–704.*

(List continued on next page.)

Primary Examiner—Thurman K. Page
Assistant Examiner—Isis Ghali
(74) Attorney, Agent, or Firm—Dann Dorfman Herrell and Skillman, P.C.

(57) ABSTRACT

A steroid is used as an additive in manufacture of a transdermal drug delivery device, to act as a crystallization inhibitor inhibiting crystallization, during storage of the device, of an active drug in the form of a hormone which has a pharmaceutical or physiological effect in use of the device. The crystallization-inhibiting steroid is present in the device in an amount insufficient to provide significant pharmaceutical or physiological effect in use of the device.

28 Claims, 2 Drawing Sheets

OTHER PUBLICATIONS

Stevenson et al., The Lancet, 335:265–269 (1990).
Whitehead et al., The Lancet, 335:310–12 (1990).
Bruce Ettinger, M.D., Obstet Gynecol 72: 5 (supplement), Nov. (1998).
Ma et al., International Journal of Pharmaceutics, 142: 115–119 (1996).
Ma et al., Intern. Symp. Control. Rel. Bioact. Mater., 22: 712–713 (1995).
Stefano et al., Int'l Symp. Control. Rel. Bioact. Mater., 24: 703–704 (1997).
Needham et al., Journal of Pharmaceutical Sciences, 81 (10): 1012–1014, Oct. (1992).
Stefano et al., Int'l. Symp. Control. Rel. Bioact. Mater., 24: 701–702 (1997).

* cited by examiner

INHIBITION OF CRYSTALLIZATION IN TRANSDERMAL DEVICES

FIELD OF THE INVENTION

This invention relates to devices for transdermal drug delivery and methods of making them. More particularly, this invention relates to the inhibition of the formation of crystals in a transdermal device such as a monolithic matrix transdermal system that delivers a hormone at therapeutically effective rates.

BACKGROUND OF THE INVENTION AND PRIOR ART STATEMENT

The transdermal route of parenteral delivery of drugs provides many advantages over other administration routes, such as slow controlled release and the avoidance of hepatic first-pass metabolism, (Stevenson et al. The Lancet, vol. 336, (1990) pp. 265). Several patent publications describe transdermal delivery devices for estradiol that are suitable for the treatment of gynaecological disorders such as climacteric disturbances and menstrual abnormalities.

For instance, U.S. Pat. No. 5518734 discloses a device for the transdermal administration of estradiol or estradiol and norethindrone acetate which includes an inhibitor of the enzymatic degradation of estradiol to estrone in the skin.

EP-A-0328806 discloses a drug-containing adhesive device for transdermal delivery system for estrogens which is free of any discrete permeable, polymeric, diffusion-controlling membrane.

WO 90/06120 patent discloses transdermal delivery of estradiol using a solvent system comprising oleic acid, linear alcohol, lactate and either dipropylene glycol or N-methyl-2-pyrrolidone. This solvent system may be used to prepare an adhesive matrix transdermal device or a reservoir transdermal device.

U.S. Pat. No. 4814168 discloses a dermal composition suitable for use in the transdermal delivery of drugs, which composition permits a high loading of a medicament. The dermal composition comprises a drug, a multi-polymer comprising vinyl acetate and ethylene monomers, a natural or synthetic rubber and a tackifying agent. WO 89/07951 discloses a pressure-sensitive adhesive sheet material for delivering estradiol to skin comprising a pressure sensitive adhesive polymer, two or more skin permeation enhancing ingredients and estradiol.

U.S. Pat. No. 5352457 discloses a method of preparing a device for transdermal delivery in which part or all the active ingredient is present in a saturated or supersaturated solution.

Protection of the endometrium from the effects of unopposed estradiol can be achieved by sequential treatment with norethisterone for two weeks of each 28-day cycle. (Ettinger B. Obstetrics and Gynaecology vol. 72, No 5 (supplement) 1988 pp. 12S, 31S, Whitehead et al. The Lancet, vol. 335, 1990 pp.310). Thus, a transdermal estradiol/norethindrone combination patch is a very desirable item.

Several documents relate to transdermal estradiol/norethindrone monolithic systems. For instance U.S. Pat. No. 5,518,734 mentioned above discloses a monolithic device system for the administration of estradiol by the transdermal route and a process of manufacturing said device; it also discloses that the system is versatile enough to allow the incorporation of a progestin such as norethindrone acetate.

U.S. Pat. No. 5,023,084 discloses a multicompartment—transdermal drug delivery system for delivery of norethindrone and estradiol. The system comprises a backing layer, an adhesive layer in which an estrogen is dissolved or microdispersed and adhered to this layer, an adhesive layer in which a progestin is also dissolved or microdispersed.

In monolithic transdermal systems, the hormone is dissolved in a pressure sensitive adhesive matrix. To deliver the desired therapeutic dose into the body, a supersaturated drug concentration is often needed. However, in such condition the system is thermodynamically unstable and the supersaturated drug has a tendency to precipitate or crystallize (Ma et al, Proceed. Intern. Symp. Control. Rel. Bioact. Mater., 22 (1995)). Therefore, control of drug crystallization is of particular interest for transdermal systems; for example, Campbell et al. resorted in the method of heating to a temperature above the melting point of a crystalline hydrate to prevent the crystallization. (U.S. Pat. No. 4,832,953)

Ma et al (Int. J. of Pharm. 142 (1996) pp. 115–119) found that PVP added to the matrix act as an effective crystallization inhibitor for norethindrone acetate transdermal delivery systems.

Also, DE-A-4210711 affirms that cholesterol and $SiO_2$ are crystallization inhibitors for 17-$\beta$-estradiol transdermal delivery system.

Another document that describes a crystal inhibitor is WO 95/18603 which affirms that soluble PVP increases the solubility of a drug without negatively affecting the adhesivity or the rate of drug delivery from the pressure-sensitive adhesive composition.

Extensive development efforts have been devoted to design the process and equipment for the manufacture of a 7-day transdermal delivery patch which comply with the required delivery therapeutic daily rates of 17-$\beta$-estradiol and norethindrone acetate and also demonstrate satisfactory long term chemical and physical stability.

In the development of transdermal delivery systems, size is an important variable to consider. To deliver an adequate therapeutic dose having an adequate size, high concentrations of hormones are commonly needed.

Drug concentration in monolithic transdermal delivery systems can vary widely depending on the drug and polymer used. High concentrations of dissolved active ingredient can be used to increase flux of the active ingredient through the skin, as is shown in several patent publications.

Failure to control crystal size and distribution can result in products whose appearance suggests that the manufacturing process by which are produced are not under control. Also, the presence of crystals can result in loss of adhesion and could cause skin irritation.

In several coating matrixes we studied, crystallization in the adhesive depends on hormone concentration. As an example, we show in Table 1 the results obtained after manufacturing the transdermal units with different hormone concentration. Similar results have been obtained by Ma et al. (Proceed. Intern. Symp. Control. Rel. Bioact. Mater. 22 (1995) 712–713). The total drug concentration is important in affecting crystal growth. As the total drug concentration was increased, more crystal formation was observed.

TABLE 1

| LOT | AMOUNT (%) OF HORMONES IN THE COATING MASS MIXTURE | CRYSTAL OBSERVATION Storage 24 months ambient conditions | CRYSTAL OBSERVATION Storage 31 months ambient conditions | CRYSTAL OBSERVATION Storage 45 months ambient conditions |
|---|---|---|---|---|
| 066 | 6 | N.D. | N.D. | N.D. |
| 066-B | 9 | + | ++ | ++ |
| 067 | 12 | ++ | +++ | +++ |

N.D. = Not Detected
+ = Less than 10 crystals. In 16 square cm
++ = Between 10 and 20 crystals. In 16 square cm
+++ = More than 20 crystals. In 16 square cm Matrix formulation: Acrylic adhesive, tackifier, oleic acid, propylene glycol, antioxidants, and hormones.

The hormones of this table are norethindrone acetate (NEA) and 17-β-estradiol (E2). Percent total hormones is NEA plus E2, and is given here as % by weight in the liquid solution before coating.

The manufacture of transdermal delivery patches containing less than 3% of active drug has been carried out for approximately seven years with no indication of the formation of any crystals, when the coating drying process was performed either in an infrared tunnel or in a hot air tunnel.

Usually the original laminate film dried in a conventional hot air tunnel exhibited no crystals or in some lots a low degree of crystallization. However when the laminate was fed through a die-cutting machine for the formation of the individual transdermal delivery patches, crystallization began around the edges of the cut with a "feather like" growth.

In the attempts to develop transdermal delivery patches that involve higher concentrations of the medicaments, we noticed that crystallization is different around the edges of the cut than in the centre or core of the patch. In the former, the crystals are usually of "feather like" shape and vary from 2 to 50 mm. However in the core or centre of matrix the crystals are less frequent, have a "cluster" shape and are not bigger than 100 μm.

In our previous work, we found that for combination patches crystallization was not only dependent on the total hormone concentration but particularly on estradiol concentration (Stefano et al., Proc. Intern. Symp. Control. Rel. Bioact. Mater.24 (1997), 703–704).

Needham et al reported (Journal of Pharm. Sci. 81,10, (1992)) that during the development of a silicone rubber implant for the delivery of 17-β-estradiol some batches of implants made from a certain lot of commercial estradiol, inexplicably developed surface crystals of estradiol after several days of storage. They concluded that one or more unidentified impurities may have had a role in the spontaneous crystal growth on the surface of the implants.

SUMMARY OF THE INVENTION

It is accordingly an object of this invention to prevent or reduce the formation of crystals in monolithic transdermal delivery systems, while achieving the desired overall performance of the patch.

It is another object of this invention to prevent or reduce formation of crystals of hormones in combination norethindrone acetate-estradiol transdermal delivery systems.

Against the background described above, it was totally unexpected when the process developed by the present inventors was tested and found successful for obtaining transdermal delivery devices with no crystals at all.

According to the invention in one aspect there is provided a method of preparing a transdermal delivery device including the steps of preparing a mixture of an active drug component in an amount intended to have a pharmaceutical or physiological effect in use of the device and a matrix-forming material, and arranging said mixture in or on a support therefor to form a matrix containing said active drug component, said active drug component being an active hormone drug or a plurality of active hormone drugs, the method being characterized by the step of mixing into at least one of said matrix-forming material and said active drug component a measured amount of a steroid, said measured amount having an effect of inhibition of crystallization of said active drug component in storage of the completed device and being an amount insufficient to provide significant pharmaceutical or physiological effect when the device is used.

According to the invention in another aspect there is provided a transdermal delivery device having a body of material and a support therefor, the body of material containing an active drug component in an amount sufficient to provide a pharmaceutical or physiological effect when the device is used, said active drug component being an active hormone drug or a plurality of active hormone drugs, said body of material further containing, as inhibitor of crystallization of said active drug component, a steroid which is not a compound normally found as an impurity with said active hormone drug or drugs or which, in the case where it is a compound which is found as an impurity with active hormone drug or drugs, is present in an amount greater than is normally formed as an impurity, said steroid being present in an amount insufficient to provide significant pharmaceutical or physiological effect when the device is used.

The invention may further be considered to consist in use of a steroid as an additive in a process of manufacture or storage of a transdermal device which steroid acts as a crystallization inhibitor inhibiting crystallization, during storage of the device, of a hormone which is present in the device in order to have a pharmaceutical or physiological effect in use of the device, said crystallization-inhibiting steroid being present in the device in an amount insufficient to provide significant pharmaceutical or physiological effect in use of the device.

The invention is generally applicable to transdermal delivery devices having an active drug in the form of a hormone to be delivered for its therapeutic effect (which will generally be called the active drug herein), and is especially applicable in adhesive matrix (monolithic) devices in which the active drug is distributed in a body of material which is an adhesive matrix which in use holds the device on the skin. It is also applicable to other transdermal delivery devices, such as those in which the active drug is held in a body of material acting as a reservoir which is not itself in contact with the skin and in which the active drug has a tendency to crystallization.

The added steroid used in the invention to inhibit crystallization can be one which is possibly present as an impurity in the active drug due to the process of drug manufacture or for any other reason. Presumably in the past such as impurity, when present, may have had an unnoticed inhibiting effect on crystallization of the active drug. In this case the concentration of the steroid is enhanced by its addition in accordance with the invention. Alternatively the added impurity is one not found as an impurity with the active drug, being for example chemically unrelated.

As a general rule impurities in a drug used in a transdermal delivery device are at a low level, e.g. at less than 3% by weight of the drug. Typically each impurity is at less than 1% by weight of the drug and often is much lower. Where in the present invention a steroid which is a possible impurity in the active drug is used as a crystallization inhibitor, it is present at a higher level than the impurity level, preferably at least 1% by weight of the active drug, more preferably at least 3% by weight of the active drug.

Considering the specific added steroids used in examples of the invention given below, it is to be noted that estriol, estrone and estradiol benzoate are not found as impurities in either testosterone or norethisterone acetate. Estriol and estradiol benzoate are not normally identified as impurities in estradiol, while estrone is always at a level of less than 0.1% by weight in estradiol.

The quantity of the crystallization-inhibiting added steroid present should in general be such that the steroid in the device has no, or no significant, physiological or pharmaceutical effect in use of the device. This may be because its amount is so small, or because its effect if any is substantially swamped by that of the active drug, or because it is itself a compound which is degraded on skin passage or is a degradation product of the active drug for example on skin passage.

Desirably the steroid added as crystallization inhibitor is selected so that it has no pharmacological or physiological effect at the concentration used for one or more of the following reasons: its intrinsic low skin permeability in the system, its low permeation with a permeation enhancer which is present in the device, its low rate of permeation due to its low concentration in the device. Although intrinsically the steroid may, if it were to pass the skin in sufficient amount, be such as to have a physiological or pharmaceutical action, in the devices of the invention due to factors such as its low intrinsic efficiency, its low concentration and the characteristics of the device; the blood level achieved, if some of it does indeed permeate, is not sufficient to evoke any response or any noticeable or significant response in the organism.

The amount of the added steroid should be selected in accordance with the particular transdermal system, and the crystallization-inhibiting amount can be found by testing. The preferred range in our invention is 0.05 to 1% by weight in the matrix containing the active drug (excluding adhesive solvents), more preferably 0.05 to 0.5%.

Relative to the weight of the active drug or total weight of active drugs in the device, the added steroid is preferably present in an amount in the range 1 to 10 weight %, more preferably 3 to 10 weight %, e.g. 4 to 10 weight %.

The minimum amount of added steroid is the minimum having some significant inhibition on crystallization and may be as low as 1/200 of the total amount of active drug but as indicated an amount greater than 1/100 is preferred.

Within the invention, a plurality of the added steroids may be used together as crystallization inhibitors.

The ranges of the added amount of crystallization inhibiting steroid here apply to a specific compound, or where more than one such compound is added, to each such compound.

In more detail, we found that by adding a low quantity of a steroid to the polymeric adhesive matrix we can control and prevent the crystal formation of the active hormone or hormones. The adding of such compounds at even 100 fold lower concentration than the active drugs concentration can in some cases prevent crystal formation. The adding of such compounds can prevent the crystal formation without adversely affecting transdermal permeation rates and in a matrix device can permit the drug-containing matrix adhesive to retain the needed adhesivity.

The adding of a steroid to the polymeric adhesive matrix may also permit increased loading of the drug in the pressure-sensitive adhesive composition. A small amount of a steroid hormone different to the saturated or supersaturated hormone is sufficient to prevent or control crystallization without affecting the overall performance of the patch.

The actual amount of steroid to be added will depend on the system and can be experimentally determined by workers skilled in the art. The maximum amount of crystal inhibitor to be added is that amount that inhibits crystallization but has low or zero biological activity and good safety toxicological behaviour.

In particularly preferred embodiments, the active drug to be transdermally administered is a hormone, such as an estrogen, a progestational agent (progestin) or a combination thereof. Although this invention will be described with respect to specific examples relating to the manufacture of transdermally delivery devices of hormones, it should be noted that this invention is applicable to the manufacture of any transdermal delivery device in which the active drug is in a saturated or supersaturated concentration. The adding of a small amount of a compound of similar but not equal structure than the saturated drug prevents or control the crystallization of the active drugs in matrix transdermal delivery devices.

As used herein, the term "hormone" and its equivalents "active drug" and "steroid hormone" are intended to have the broadest meaning as including any therapeutically, and/or pharmacologically or physiologically hormone, or mixture thereof, which is delivered to a living organism to produce a desired, usually beneficial effect.

Exemplary of drugs that can be administered by the novel transdermal system of this invention include, but are not limited to:

Estrogens, including:
  nonsteroidal estrogens such as benzestrol, broparoestrol, chlorotrianisene, dienestrol, diethylstilboestrol, diethylstilboestrol dipropionate, dimestrol, fosfestrol, hexoestrol, methallenestril and methestrol, and steroidal estrogens as colpormon, conjugated estrogenic hormones, equilenin, equilin, estradiol, estriol, estrone, ethinyl estradiol, estradiol benzoate, mestranol, moxestrol, mytatrienediol, quinestradiol, quinestrol.

Progestogens such as allylestrenol, anagestone, chlormardinone acetate, delmadinone acetate, demegestone, desogestrel, dimethisterone, drospirenone, dydrogesterone, ethisterone, ethynodiol, flurogestone acetate, gestodene, gestonorone caproate, 17-hydroxy-16-methylene-δ-progesterone, 17α hydroxyprogesterone, lynestrenol, medrogestone, medroxyprogesterone, megestrol acetate, melengestrol, norethindrone, norethindrone acetate, norethynodrel, norgesterone, norgestimate, norgestrel, norgestrienone, norvinisterone, pentagestrone, progesterone, promegestone, trengestone.

Androgens such as boldenone, cloxotestosterone, fluoxymesterone, mestanolone, mesteronolone, 17-methyltestosterone, 17α-methyltestosterone 3-cyclopentyl enol ether, norethandrolone, normethandrone, oxandrolone, oxymesterone, oxymetholone, prasterone, stanolone, stanolozol, testosterone, tiomesterone.

Glucocorticoids such as 21-acetoxypregnenolone, alclometasone, algestone, amcinonide, beclomethasone, bethamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, flucinolone acetonide, fluocinonide, fluocortin butyl, fluocortolone, fluorometholone, fluperolone acetate, fluprednidene acetate, fluprednisolone, flurandrenolide, fluticasone propionare, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylaminoacetate, prednisolone sodium phosphate, prednisone, prednival, prednylidene, rimexolone, tixocortol, triamcinolone, triamcinolone acetonide, triamcinolone benetonide, triamcinolone hexacetonide.

The adhesive material may be selected from a wide variety of pressure sensitive adhesive materials such as silicones, rubber, polyisobutylene, and acrylic adhesives. Exemplary of acrylic adhesives that can be used by this novel transdermal system of this invention include, but are not limited to:

Acrylic adhesives such as the range of polyacrylate adhesives sold under the trademark Duro-Tak 80–1194, 80–1196,80–1197,2287,2516 2852, 387–2051, 387–2052, 387–2054, 387–2287, 387–2353, 387–2510, 387–2516, 387–2620, 387–2825, 387–2070, 87–2074, 87–2097, 87–2100, 87–2154, 87–2194, 87–2196, 87–2852 and 87–2979 by National Starch and Chemical Corporation, Bridgewater, N.J., USA. Other suitable acrylic adhesives are those sold under the trademark Gelva—Multipolymer Solution GMS 737, 788, 263, 1151, 1159, 1430, 1753, 2450, 2465, 2480, 2495, 2497 and 2539 by Monsanto, St Louis, Mo. USA.

Crosslinkers as for example those sold under the name of Resimene (Monsanto Chemical Co., ST Louis Mo.), titanium butoxide, and Aluminum acetyl acetonate can be added to the adhesive matrix.

A permeation enhancer or a combination of permeation enhancers can be included to the adhesive matrix. These enhancers could be but are not limited to: oleic acid, propylenglycol, ethyl oleate, oleyl alcohol, oleyl amide, mygliol, isopropyl miristate, isopropyl palmitate and DEET.

A reinforcing component (solid) may be employed and may be selected from the polyterpene resins, such as modified colophony resins such as Pentalyn A. and Pentalyn H (Hercules Inc.) (an esterified colophony resin with pentaeritritol).

Amongst materials suitable for the flexible substrate (cellulose xantate film), Saran (polyvinylidene chloride film), polyvinyl chloride, polyethylene, polypropylene, polyurethane, polyesters such as polyethylene terephtalate including binary structures such as aluminum-polyethylene coatings, etc, may be used.

For the releasable protective layer, any of the above mentioned coatings for the substrate can be used, preferably polyesters, such as polyethylene terephthalate, etc. covered with a silicone to prevent sticking of the adhesive.

The packaging could be either of a blister or a pouch type. The material of the packaging should be moisture impermeable. For added moisture protection a desiccant can be added to the packaging.

EXAMPLES

The following specific examples are provided as exemplary of the invention but are not limitative.

General Experimental Details

A) Preparation of the Adhesive Mixture

To a vinyl-acrylic multi polymer adhesive solution diluted with ethanol, toluene, ethyl acetate to 31–34% wt. solids, a solid rosin tackifier component is added with stirring at room temperature for a period of time necessary to obtain a homogeneous mixture.

B) Preparation of Formula Containing the Active Drug

To the material prepared in step A), while stirring, the active drug or combination of active drugs, antioxidants, oleic acid and propylene glycol are added. When appropriate a crystallization inhibitor is added. A clear solution is obtained and kept in a closed vessel to avoid evaporation of the solvent medium.

C) Preparation of the Transdermal Delivery System

On a release liner (a polyester film with a silicone layer), the solution prepared as described above, is applied by means of a conventional coating device. The solution is applied to the siliconized surface. Then it is dried by infra red lamps or by hot air circulation to obtain a layer of final thickness 80–110 μm. Then, this coated siliconized polyester is laminated on a second flexible film which constitutes the backing in the finished device. The process ends with cutting to size, for example by means of a die cutting of the multilayer laminate to form shapes of the desired geometry and size. When packaging took place, the final product is packaged in a thermoformed PVC-aluminium blister system or in an aluminum pouch, which is heat sealed with a lacquered aluminum foil laminate. The package may contain a water desiccant inside.

D) Holding Power/Shear Adhesion Test

The holding power/shear adhesion is the ability of pressure sensitive tapes to remain adhered under load applied parallel to the surfaces of the tape. It is a measure of a combination of adhesive and cohesive strengths of an adhesive. (Pressure Sensitive Tape Council "Test methods for pressure sensitive adhesive tapes", 1996) It is expressed as the time required for a given weight to cause a given area of adhesive to come loose from a vertical panel. In this work, a 1 pound (0.45 kg) weight is attached to a strip of adhesive matrix attached to a steel panel. Since this "holding power" test is highly dependent on the area of adhesive contacting the test panel, ½ inch square (3 cm²) surface strip was used in all cases. A rack holds the panel 0° from vertical, with tape applied at an angle of 0° with the vertical, so that when the mass is acting on the test specimen, no peel forces will be exerted on the tape. The shear test was conducted at ambient conditions (25±2° C., 75%; relative humidity).

In all the Examples following, the composition of the formula is expressed in weight percent of the total content of the adhesive coating, i.e. excluding adhesive solvents, but including material such as propylene glycol and oleic acid.

Example 1

Norethindrone acetate and estradiol transdermal delivery system.

In this example the quantities used were:

| Formula a | |
|---|---|
| Adhesive polymer | 45.35% |
| Tackifier | 20% |
| Norethindrone acetate | 7.5% |
| Estradiol | 1.5% |
| Propyleneglycol | 15% |
| Oleic acid | 10% |
| Antioxidants | 0.55% |
| Estriol | 0.1% |
| Formula b | |
| Adhesive polymer | 45.45% |
| Tackifier | 20% |
| Norethindrone acetate | 7.5% |
| Estradiol | 1.5% |
| Propyleneglycol | 15% |
| Oleic acid | 10% |
| Antioxidants | 0.55% |

Results

Crystal observation of patches stored without packaging at 40° C. 75% relative humidity 30 days after day of manufacture.

| | Crystal observation |
|---|---|
| Formula a | Crystals not detected |
| Formula b | Feather growth crystals of approx. 7 mm |

The above data clearly show that the crystal formation in a NEA-E2 transdermal patch can be prevented by the addition of a small quantity of an estrogen (estriol 0.1% in this example).

Example 2

Norethindrone acetate and estradiol transdermal delivery system.

The composition is similar to Example 1, as follows:

| Formula a | |
|---|---|
| Adhesive polymer | 45.35% |
| Tackifier | 20% |
| Norethindrone acetate | 7.5% |
| Estradiol | 1.5% |
| Propyleneglycol | 15% |
| Oleic acid | 10% |
| Antioxidants | 0.55% |
| Estrone | 0.1% |
| Formula b | |
| Adhesive polymer | 45.45% |
| Tackifier | 20% |
| Norethindrone acetate | 7.5% |
| Estradiol | 1.5% |
| Propyleneglycol | 15% |
| Oleic acid | 10% |
| Antioxidants | 0.55% |

Results

Crystal observation of patches stored without packaging at 40° C. 75% relative humidity 120 days after day of manufacture.

| | Crystal observation |
|---|---|
| Formula a | Crystals not detected |
| Formula b | Feather growth crystals of approx. 8 mm |

The above data clearly show that the crystal formation in a NEA-E2 transdermal patch can be prevented by the addition of a small quantity of an estrogen (estrone 0.1% in this example).

Example 3

Norethindrone acetate and estradiol transdermal delivery system.

In this example the quantities used were:

| Formula a | |
|---|---|
| Adhesive polymer | 45.9% |
| Tackifier | 20% |
| Norethindrone acetate | 6.9% |
| Estradiol | 1.5% |
| Propyleneglycol | 15% |
| Oleic acid | 10% |
| Antioxidants | 0.1% |
| Norethindrone | 0.6% |
| Formula b | |
| Adhesive polymer | 45.9% |
| Tackifier | 20% |
| Norethindrone acetate | 7.5% |
| Estradiol | 1.5% |
| Propyleneglycol | 15% |
| Oleic acid | 10% |
| Antioxidants | 0.1% |

Results

Crystal observation of patches stored in a PVC-aluminium blister without desiccant at 40° C. 75% relative humidity 1 year after day of manufacture.

|  | Crystal observation |
|---|---|
| Formula a | Crystals not detected |
| Formula b | Feather growth crystals of approx. 15 mm |

The above data clearly show that the crystal formation in a NEA-E2 transdermal patch can be prevented by the addition of a small quantity of a progestin (norethindrone 0.6% in this example). It can be assumed that norethindrone has no pharmaceutical or physiological effect at this level, due to its low concentration and its low permeation inherently and in comparison with norethindrone acetate in this device.

Example 4

Norethindrone acetate and estradiol transdermal delivery system.

In this example the quantities used were:

| Formula a | |
|---|---|
| Adhesive polymer | 45.35% |
| Tackifier | 20% |
| Norethindrone acetate | 7.5% |
| Estradiol | 1.5% |
| Propyleneglycol | 15% |
| Oleic acid | 10% |
| Antioxidants | 0.55% |
| Estradiol benzoate | 0.1% |
| Formula b | |
| Adhesive polymer | 42.95% |
| Tackifier | 20% |
| Norethindrone acetate | 7.5% |
| Estradiol | 1.5% |
| Propyleneglycol | 15% |
| Oleic acid | 10% |
| Antioxidants | 0.55% |
| PVP K30 | 2.5% |
| Formula c | |
| Adhesive polymer | 44.45% |
| Tackifier | 20% |
| Norethindrone acetate | 7.5% |
| Estradiol | 1.5% |
| Propyleneglycol | 15% |
| Oleic acid | 10% |
| Antioxidants | 0.55% |
| $SiO_2$ | 0.7% |
| MgO | 0.3% |

Results

Crystal observation of patches stored in an aluminium pouch with a water desiccant at 25° C. with 60% relative humidity outside the patch, 60 days after day of manufacture.

|  | Crystal observation |
|---|---|
| Formula a | Crystals not detected |
| Formula b | Feathers 2 mm |
| Formula c | Feathers 4 mm |

The above data clearly show that the crystal formation in a NEA-E2 transdermal patch can be prevented by the addition of a small quantity of an estrogen (estradiol benzoate 0.1% in this example). In these experimental conditions, this estrogen prove to be a better crystal inhibitor than PVP (a well known crystal inhibitor in pharmaceutical use) and $SiO_2$ (as proposed in DE-A-4210711).

Example 5

Estradiol transdermal delivery system

Two different estradiol concentrations and control formulations in an acrylic adhesive were evaluated.

|  | with crystal growth inhibitor | control |
|---|---|---|
| Formula a | | |
| Adhesive polymer | 51.35% | 51.45% |
| Tackifier | 20% | 20% |
| Propylene glycol | 15% | 15% |
| Oleic acid | 10% | 10% |
| Antioxidants | 0.55% | 0.55% |
| Estradiol | 3% | 3% |
| Estrone | 0.1% | — |
| Formula b | | |
| Adhesive polymer | 50.35% | 50.45% |
| Tackifier | 20% | 20% |
| Propylene glycol | 15% | 15% |
| Oleic acid | 10% | 10% |
| Antioxidants | 0.55% | 0.55% |
| Estradiol | 4% | 4% |
| Estrone | 0.1% | — |

Results

Crystal observations of patches stored without packaging at 40° C., 75% relative humidity.

|  | Crystal observation |
|---|---|
| Formula a (90 days after day of manufacture) | |
| with crystal growth inhibitor | Crystals not detected |
| control | Feather growth crystals of approx. 7 mm |
| Formula b (45 days after day of manufacture) | |
| with crystal growth inhibitor | Crystals not detected |
| control | Feather growth crystals of approx. 9 mm |

The above data show that the crystal formation in a patch containing only estradiol as active hormone can be prevented by the addition of a small quantity of an estrogen (estrone 0.1% in this example).

Besides, as seen by Ma. et. al. (Proceed. Intern. Symp. Control Rel. Bioact. Mater. 22 (1995) 712–713) the rate of drug crystallization increased with the increase of drug concentration comparing the control of formula a with the control of formula b. However, 0.1% of estrone prevented crystallization of estradiol in both formulations.

Example 6

Testosterone transdermal delivery system.

In this example the quantities used were:

| Formula a | |
|---|---|
| Adhesive polymer | 84.9% |
| Testosterone | 7.5% |
| Enhancer | 7.5% |
| Estrone | 0.1% |
| Formula b | |
| Adhesive polymer | 85% |
| Testosterone | 7.5% |
| Enhancer | 7.5% |

Results

Crystal observation of patches stored without packaging at 40° C. 75% relative humidity 15 days after day of manufacture.

| Crystal observation | |
|---|---|
| Formula a | Crystals not detected |
| Formula b | Crystals of approx. 1 mm |

The above data clearly show that the crystal formation in a testosterone transdermal patch can be prevented by the addition of a small quantity of an estrogen (estrone 0.1% in this example).

Example 7

Norethindrone acetate and Estradiol transdermal delivery system.

The composition is similar to Example 1:

| Formula a | |
|---|---|
| Adhesive polymer | 60.35% |
| Tackifier | 20% |
| Norethindrone acetate | 7.5% |
| Estradiol | 1.5% |
| Oleic acid | 10% |
| Antioxidants | 0.55% |
| Estrone | 0.1% |
| Formula b | |
| Adhesive polymer | 60.45% |
| Tackifier | 20% |
| Norethindrone acetate | 7.5% |
| Estradiol | 1.5% |
| Oleic acid | 10% |
| Antioxidants | 0.55% |

Results

Crystal observation of patches stored without packaging at 40° C. 75% relative humidity 90 days after day of manufacture.

| Crystal observation | |
|---|---|
| Formula a | Crystals not detected |
| Formula b | Feather growth crystals of approx. 8 mm |

The above data clearly show that the crystal formation in a NEA-E2 transdermal patch can be prevented by the addition of a small quantity of an estrogen (estrone 0.1% in this example).

Example 8

Effect of Drug Concentrations

Drug concentrations from 8.25 to 12% of total (w/w) were evaluated in an acrylic adhesive. The size of the crystals was measured. The hormone contents were

| Formula a | 8.25% total | NEA 7%, estradiol 1.25% |
| Formula b | 9% total | NEA 7.5%, estradiol 1.5% |
| Formula c | 10.5% total | NEA 8.75%, estradiol 1.75% |
| Formula d | 12% total | NEA 10%, estradiol 2%. |

| | Estrone | Control |
|---|---|---|
| Formula a | | |
| Adhesive polymer | 46.1% | 46.2% |
| Tackifier | 20% | 20% |
| Norethindrone acetate | 7.0% | 7.0% |
| Estradiol | 1.25% | 1.25% |
| Propyleneglycol | 15% | 15% |
| Oleic acid | 10% | 10% |
| Antioxidants | 0.55% | 0.55% |
| Estrone | 0.1% | — |
| Formula b | | |
| Adhesive polymer | 45.35% | 45.45% |
| Tackifier | 20% | 20% |
| Norethindrone acetate | 7.5% | 7.5% |
| Estradiol | 1.5% | 1.5% |
| Propyleneglycol | 15% | 15% |
| Oleic acid | 10% | 10% |
| Antioxidants | 0.55% | 0.55% |
| Estrone | 0.1% | — |
| Formula c | | |
| Adhesive polymer | 43.85% | 43.95% |
| Tackifier | 20% | 20% |
| Norethindrone acetate | 8.75% | 8.75% |
| Estradiol | 1.75% | 1.75% |
| Propyleneglycol | 15% | 15% |
| Oleic acid | 10% | 10% |
| Antioxidants | 0.55% | 0.55% |
| Estrone | 0.1% | — |
| Formula d | | |
| Adhesive polymer | 42.35% | 42.45% |
| Tackifier | 20% | 20% |
| Norethindrone acetate | 10.0% | 10.0% |
| Estradiol | 2.0% | 2.0% |
| Propyleneglycol | 15% | 15% |
| Oleic acid | 10% | 10% |
| Antioxidants | 0.55% | 0.55% |
| Estrone | 0.1% | — |

Figure 1:
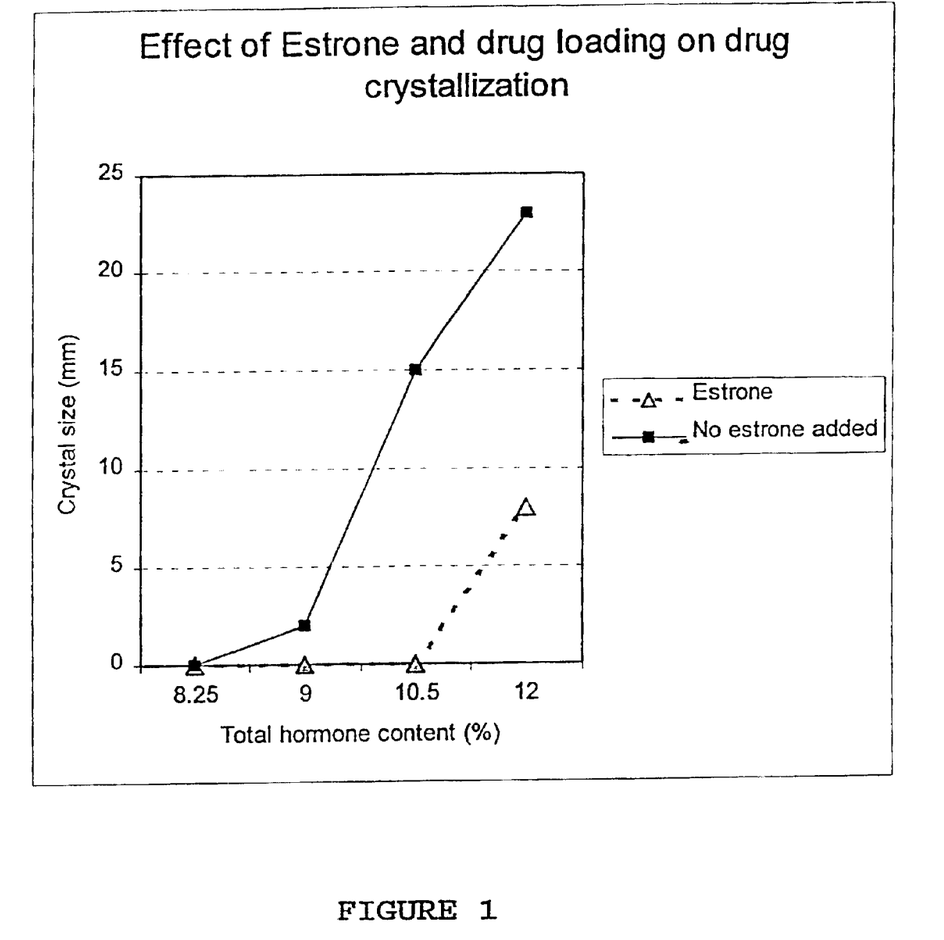
FIG. 1 is a graph plotting drug crystallization data obtained in Example 8 described below.

As is also shown in Example 5 above, the rate of drug crystallization increased with the increase of drug concentration. FIG. 1 shows that estrone 0.1% weight was effective to inhibit totally crystallization up to a total hormone concentration of 10.5%. Up to 10.5% of total drug with estrone 0.1% no drug crystals were detected microscopically up to 1 month of storage without packaging at accelerated crystallization conditions (40° C., 75% R.H.). At 12% of total drug with estrone 0.1% the rate and the number of crystals was significantly lower than for the controls without estrone.

Example 9

This example shows that the patches with the crystal inhibitor added show similar results in the shear test. The devices contained NEA 7.5% and estradiol 1.5% as active drugs. The formulations were

|  | Control | Estrone | Estradiol Benzoate | Norethindrone |
|---|---|---|---|---|
| Adhesive polymer | 45.45% | 45.35% | 45.35% | 45.35% |
| Tackifier | 20% | 20% | 20% | 20% |
| Norethindrone acetate | 7.5% | 7.5% | 7.5% | 7.5% |
| Estradiol | 1.5% | 1.5% | 1.5% | 1.5% |
| Propyleneglycol | 15% | 15% | 15% | 15% |
| Oleic acid | 10% | 10% | 10% | 10% |
| Antioxidants | 0.55% | 0.55% | 0.55% | 0.55% |
| Crystal inhibitor | None | 0.1% | 0.1% | 0.1% |

| Formula | Shear test (sec) |
|---|---|
| Control (without crystal inhibitors added) | 273 ± 20 |
| estrone 0.1% | 253 ± 20 |
| estradiol benzoate 0.1% | 282 ± 20 |
| norethindrone 0.1% | 310 ± 20 |

Example 10

Norethindrone acetate and estradiol transdermal delivery system.

The composition is again similar to Example 1:

| Formula a | |
|---|---|
| Adhesive polymer | 45.35% |
| Tackifier | 20% |
| Norethindrone acetate | 7.5% |
| Estradiol | 1.5% |
| Propyleneglycol | 15% |
| Oleic acid | 10% |
| Antioxidants | 0.55% |
| Hydrocortisone acetate | 0.1% |
| Formula b | |
| Adhesive polymer | 45.45% |
| Tackifier | 20% |
| Norethindrone acetate | 7.5% |
| Estradiol | 1.5% |
| Propyleneglycol | 15% |
| Oleic acid | 10% |
| Antioxidants | 0.55% |

Results

Crystal observation of patches stored without packaging at 40° C. 75% relative humidity 30 days after day of manufacture.

| Crystal observation | |
|---|---|
| Formula a | Crystals not detected |
| Formula b | Feather growth crystals of approx. 2 mm |

The above data clearly show that the crystal formation in a NEA-E2 transdermal patch can be prevented by the addition of a small quantity of hormone (hydrocortisone acetate 0.1% in this example)

Example 11

Norethindrone acetate and estradiol transdermal delivery system (made with purified estradiol).

The composition is as follows:

In formula a the estradiol used corresponded to a commercial lot of Schering AG without further purification. In Formula b the same estradiol was previously purified by recrystallization.

| Formula a | |
|---|---|
| Adhesive polymer | 45.45% |
| Tackifier | 20% |
| Norethindrone acetate | 7.5% |
| Propyleneglycol | 15% |
| Estradiol | 1.5% |
| Oleic acid | 10% |
| Antioxidants | 0.55% |

Schering AG report that the main impurities in its estradiol are:

Δ9 -estradiol: n.d. (not detectable)–0.05% estrone: n.d.–0.05%

4-methyl estradiol: 0.24–0.48%

| Formula b | |
|---|---|
| Adhesive polymer | 45.45% |
| Tackifier | 20% |
| Norethindrone acetate | 7.5% |
| Propyleneglycol | 15% |
| Estradiol | 1.5% |
| Oleic acid | 10% |
| Antioxidants | 0.55% |

Results

Figure 2:
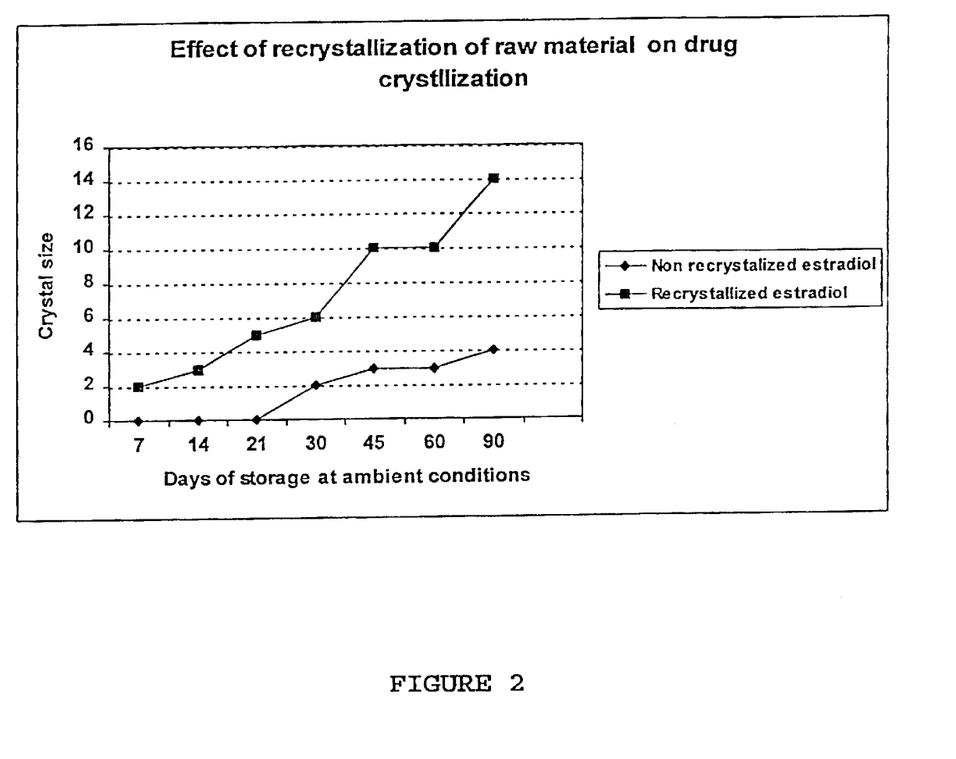
FIG. 2 is a graph plotting drug crystallization data obtained in Example 11 described below.

FIG. 2 shows that the crystal growth in a NEA-E2 transdermal patch made with the recrystallized estradiol was bigger than with the non-recrystallized estradiol, or storage in ambient conditions without packaging. Since this commercial lot of estradiol contained small quantities of other steroids as impurities, it can be concluded that the small quantities of these impurities present in the raw material had some delaying effect on crystal growth. The addition of more steroids as proposed in previous examples further stabilizes the matrix patch.

Example 12

Effect of different adhesive polymers.

The use of four different commercial adhesive polymers was evaluated in a matrix that contains estradiol as the active drug and estrone as the crystal growth inhibitor. For each adhesive, two different storage conditions were also evaluated.

| General formula | |
| --- | --- |
| Adhesive polymer | 84.6% |
| Tackifier | 10% |
| Antioxidants | 1.6% |
| Estradiol | 3.5% |
| Estrone | 0.3% |

The characteristics of the different pressure sensitive adhesives (PSA) are

| | Functional groups of the acrylic PSA | Manufacturing Company |
| --- | --- | --- |
| Formula a | —COOH/—OH | National Starch and Chemical Company |
| Formula b | —COOH | National Starch and Chemical Company |
| Formula c | —OH | National Starch and Chemical Company |
| Formula d | —OH | Monsanto |

Results

Crystal observations of matrices stored at 25° C., 60% relative humidity with and without humidity protection 180 days after day of manufacture.

For humidity protection, the matrix was enclosed in a sealed aluminium pouch with a desiccant.

| | Crystal observation | |
| --- | --- | --- |
| | without a humidity protector | with a humidity protector |
| Formula a | Crystals not detected | Crystals not detected |
| Formula b | Clusters of 1 mm | Crystals not detected |
| Formula c | Clusters of 1 mm | Crystals not detected |
| Formula d | Clusters of 1 mm | Crystals not detected |

The above data show that none of the observed matrices formulated with a small quantity of estrone, have crystals bigger than 1 mm or with feather shape. However, the use of different adhesives shows different performances, the best being the one with —COOH/—OH as functional groups. Prevention of humidity enhances the protective effect of the crystal growth inhibitor used.

What is claimed is:

1. A method of preparing a transdermal delivery device comprising the steps of:
   (a) preparing a mixture of:
      (i) an active drug component,
      (ii) a matrix-forming material, and
      (iii) a measured amount of a steroid hormone, and
   (b) applying said mixture to a support to form on said support a matrix containing said active drug component,
   said step (a) including mixing said measured amount of said steroid hormone with said active drug component and said matrix-forming material, wherein:
      said active drug component is at least one active hormone drug present in said matrix in an amount having a pharmaceutical or physiological effect when the transdermal delivery device is used;
      said active hormone drug is present in said matrix at a concentration such that said matrix is one of saturated and supersaturated therewith;
      said steroid hormone is different from any said active hormone drug present in said matrix; and
      said steroid hormone being effective to inhibit crystallization of said active drug component during storage of the transdermal delivery device, and said measured amount of said steroid hormone present in said matrix providing no significant pharmaceutical or physiological effect when said device is used.

2. A transdermal delivery device having:
   a support;
   a matrix on said support;
   wherein said matrix comprises:
      (i) an active drug component,
      (ii) a matrix-forming material, and
      (iii) a steroid hormone, and
   said active drug component is at least one active hormone drug present in said matrix in an amount having a pharmaceutical or physiological effect when the transdermal delivery device is used;
   said active hormone drug is present in said matrix at a concentration such that said matrix is one of saturated and supersaturated therewith;
   said steroid hormone is different from any said active hormone drug present in said matrix and fulfils one of the following conditions:
      (a) it is not a compound normally found as an impurity in said at least one active hormone drug present in said matrix,
      (b) it is a compound found as an impurity in said at least one active hormone drug present in said matrix,
   said steroid hormone is present in said matrix in an amount which is effective to inhibit crystallization of said active drug component during storage of said transdermal delivery device but provides no significant pharmaceutical effect when said transdermal delivery device is used, and in the case where said steroid hormone fulfils said condition (b), it is present in an amount, relative to said active hormone drug in which it is found as an impurity, greater than the amount at which it is normally found as an impurity therein.

3. A method according to claim 1, wherein said matrix forming material is an adhesive.

4. A method according to claim 1, including the steps of forming a solution of said active drug component and said matrix-forming material in at least one solvent, adding said measured amount of said steroid hormone to said solution, applying said solution to a support sheet and at least partially removing said at least one solvent.

5. A method according to claim 1, wherein said at least one active hormone drug is selected from an estrogen, a progestin, an androgen and a glucocorticoid.

6. A method according to claim 1, wherein a plurality of said active hormone drugs is included in said active drug component.

7. A method according to claim 1, wherein said steroid hormone acting as crystallization inhibitor is selected from an estrogen, a progestogen, an androgen and a glucocorticoid.

8. A method according to claim 7, wherein the steroid hormone acting as crystallization inhibitor is selected from estrone, estriol, estradiol benzoate, norethindrone and hydrocortisone acetate.

9. A method according to claim 8, wherein said active drug component comprises estradiol and said steroid hormone acting as crystallization inhibitor is estrone.

10. A method according to claim 8, wherein said active drug component comprises norethindrone acetate and 17β-estradiol, and said steroid hormone acting as crystallization inhibitor is estrone.

11. A method according to claim 8, wherein said active drug component is testosterone and steroid hormone acting as crystallization inhibitor is estrone.

12. A method according to claim 1, wherein said measured amount of said steroid hormone is such, that in said device when ready for use, the amount of said steroid hormone in said matrix is in the range 0.05 to 1% by weight of total content excluding adhesive solvents.

13. A method according to claim 12, wherein said amount of said steroid hormone in said matrix is in the range 0.05–0.5% by weight of total content excluding adhesive solvents.

14. A method according to any claim 1, wherein said measured amount of said steroid hormone is such that in the device when ready for use the amount thereof present is in the range 1 to 10% by weight relative to the total weight of said at least one active hormone drug.

15. A method according to claim 1, including the further step of packaging the delivery device in an air-tight package which also contains a desiccant.

16. A transdermal delivery device according to claim 2, which is contained in an air-tight package which also contains a desiccant.

17. A transdermal delivery device according to claim 2, wherein said matrix is a coating layer intended to contact the skin in use of the device.

18. A transdermal delivery device according to claim 17, wherein said matrix comprises an adhesive.

19. A transdermal delivery device according to claim 2, wherein said at least one active hormone drug is selected from an estrogen, a progestin, an androgen and a glucocorticoid.

20. A transdermal delivery device according to claim 2, wherein a plurality of said active hormone drugs is included in said matrix.

21. A transdermal delivery device according to claim 2, wherein said steroid hormone acting as crystallization inhibitor is selected from an estrogen, a progestogen, an androgen and a glucocorticoid.

22. A transdermal delivery device according to claim 21, wherein the steroid hormone acting as crystallization inhibitor is selected from estrone, estriol, estradiol benzoate, norethindrone and hydrocortisone acetate.

23. A transdermal delivery device according to claim 22, wherein said active drug component comprises estradiol and said steroid hormone acting as crystallization inhibitor is estrone.

24. A transdermal delivery device according to claim 22, wherein as said active drug component comprises norethindrone acetate and 17β-estradiol, and said steroid hormone acting as crystallization inhibitor is estrone.

25. A transdermal delivery device according to claim 22, wherein said active drug component is testosterone and said steroid hormone acting as crystallization inhibitor is estrone.

26. A transdermal delivery device according to claim 2, wherein said amount of said steroid hormone in said device is in the range 0.05 to 1% by weight of the total content of said matrix excluding adhesive solvents.

27. A transdermal delivery device according to claim 26, wherein said amount of said steroid hormone in said device is in the range 0.05–0.5% by weight of the total content of said matrix excluding adhesive solvents.

28. A transdermal delivery device according to claim 2, wherein the amount of said steroid hormone in said matrix is 1 to 10% by weight relative to the total weight of said at least one active hormone drug.

* * * * *